United States Patent [19]
Quigley, Jr. et al.

[11] Patent Number: 5,650,171
[45] Date of Patent: Jul. 22, 1997

[54] RETINOIC ACID-CONTAINING POLYETHER-POLYURETHANE COMPOSITIONS

[75] Inventors: John W. Quigley, Jr., Foster City; Harris Goodman, San Francisco, both of Calif.

[73] Assignee: Penederm, Inc., Foster City, Calif.

[21] Appl. No.: 875,772

[22] Filed: Apr. 29, 1992

[51] Int. Cl.$^6$ ............................ A61K 31/785; A61K 9/10
[52] U.S. Cl. ..................... 424/486; 424/78.05; 514/859; 514/974
[58] Field of Search ..................... 424/401, 486, 424/78.02, 78.03, 78.05, 78.37, 59; 514/827, 828, 848, 859, 861, 863, 944, 969, 974, 946; 528/65, 66, 67

[56] References Cited

U.S. PATENT DOCUMENTS

| | | | |
|---|---|---|---|
| 3,906,108 | 9/1975 | Felty | 514/970 |
| 4,247,547 | 1/1981 | Marks | 424/78.05 |
| 4,826,677 | 5/1989 | Mueller et al. | 424/78.05 |
| 4,971,800 | 11/1990 | Chess et al. | 424/449 |

Primary Examiner—Edward J. Webman
Attorney, Agent, or Firm—Cooley Godward LLP

[57] ABSTRACT

Novel retinoic acid-containing topical compositions in the form of creams, lotions, gels, and the like, are disclosed. These compositions contain a urethane compound having a molecular weight of up to about 60,000, prepared by reacting approximately two moles of a hydroxy-terminated linear alkylene or polyalkylene glycol with approximately one mole of a monomeric organic diisocyanate. The presence of the urethane compound leads to decreased percutaneous transmission of the retinoic acid, resulting in reduced skin irritation but undiminished therapeutic effectiveness of the retinoic acid when compared to retinoic acid-containing topical formulations otherwise identical except for the absence of a urethane compound. The compositions of this invention can be used to treat acne vulgaris and ameliorate photoaging of the skin, to retard and reverse the effects of senile keratosis, and to treat a variety of other skin conditions, such as hyperpigmentation and psoriasis, hitherto considered unsuitable for treatment with retinoic acid.

7 Claims, 4 Drawing Sheets

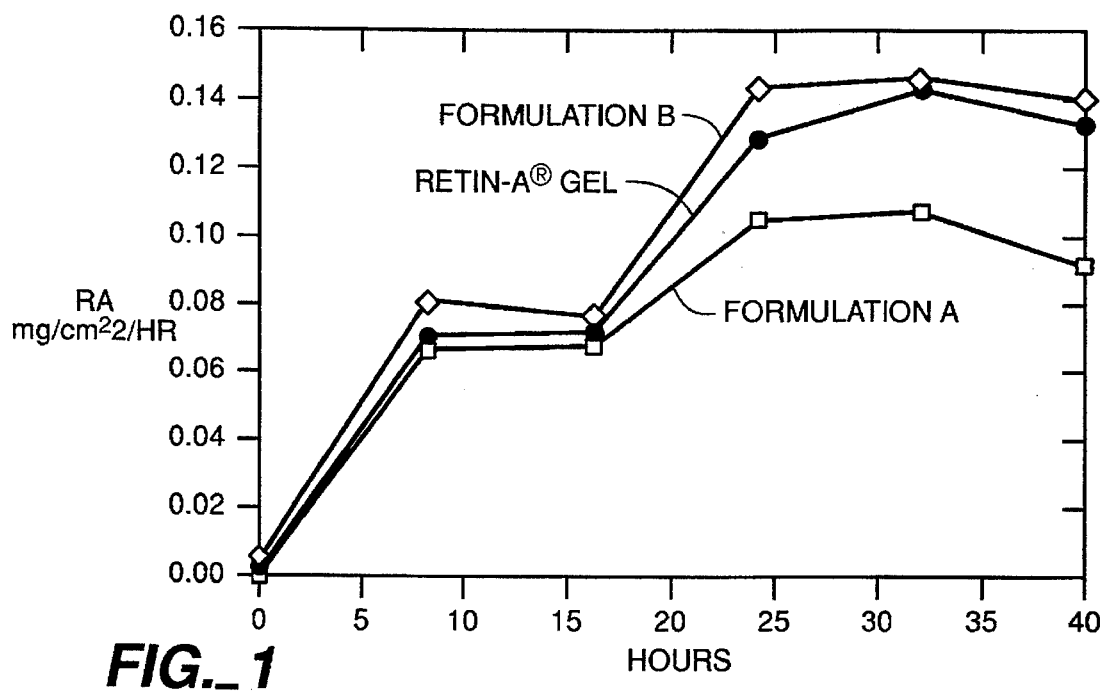
FIG._1
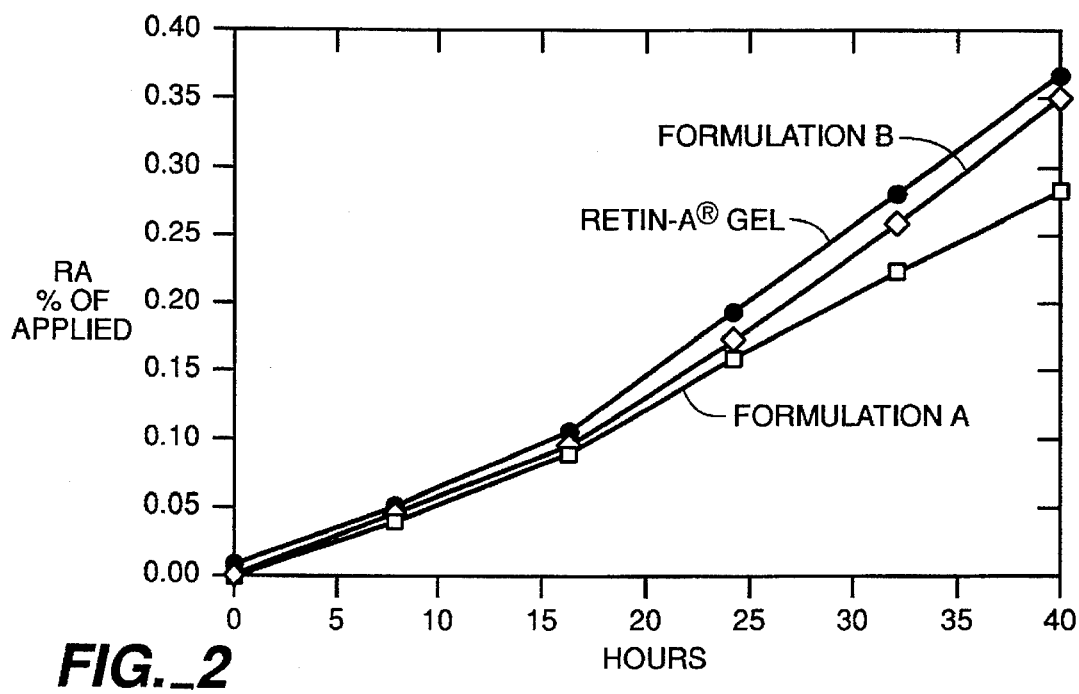
FIG._2

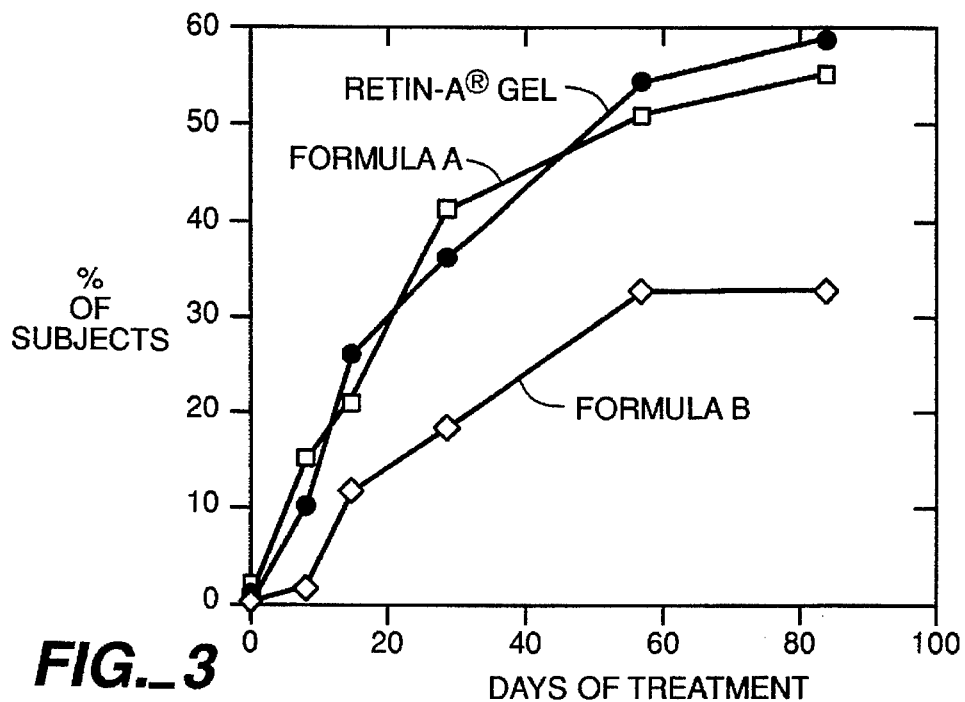
FIG._3
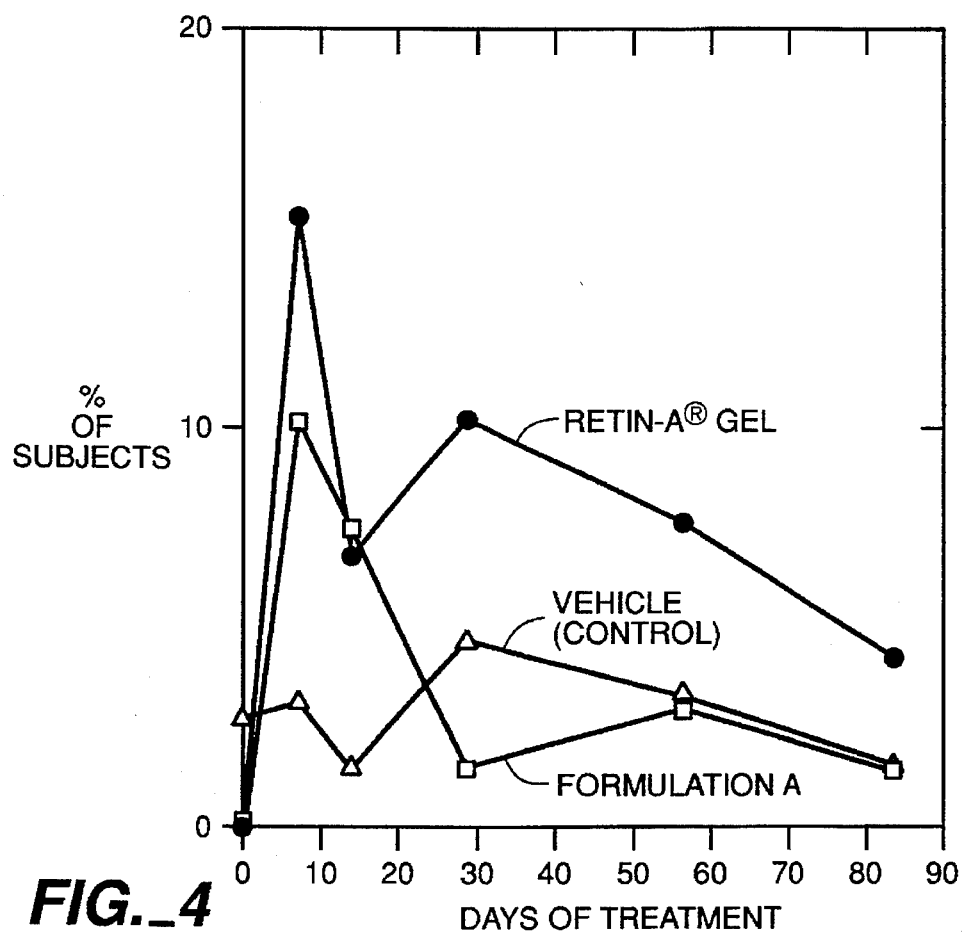
FIG._4

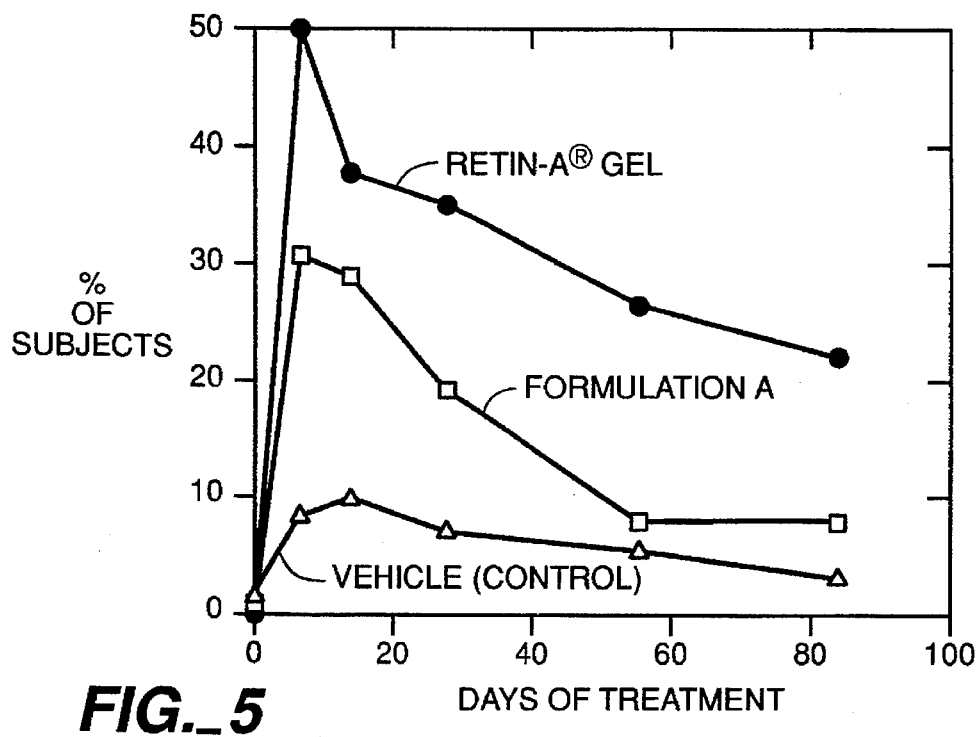
FIG._5
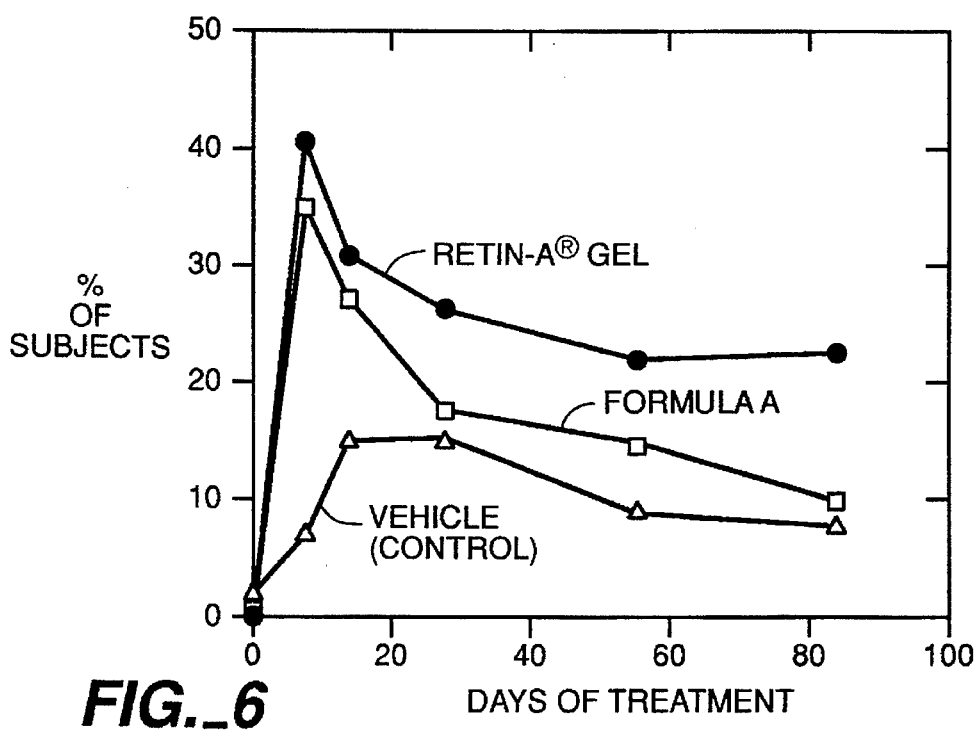
FIG._6

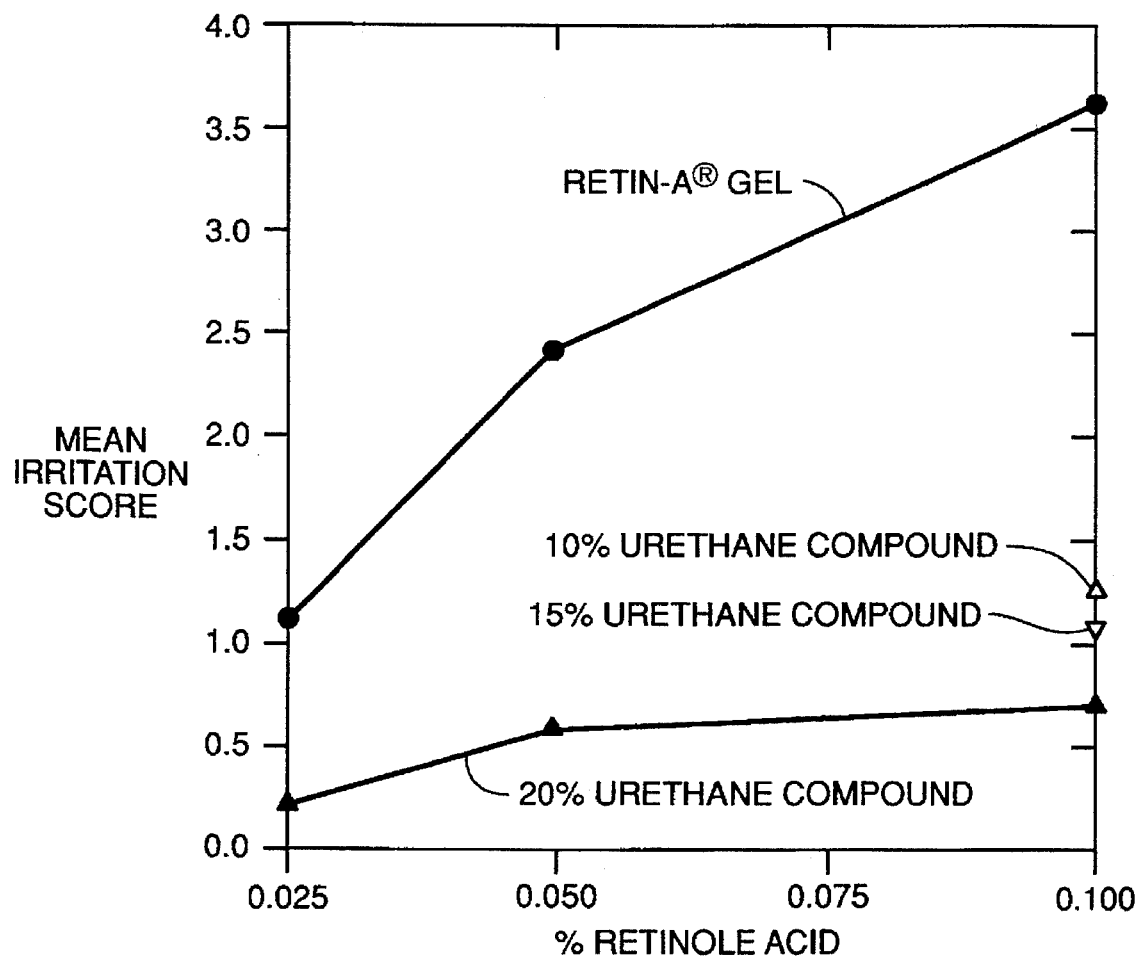
FIG._7

RETINOIC ACID-CONTAINING POLYETHER-POLYURETHANE COMPOSITIONS

BACKGROUND OF THE INVENTION

1. Field of the Invention

This invention relates to retinoic acid-containing compositions. More particularly, this invention relates to retinoic acid-containing topical compositions for use in treating, inter alia, acne vulgaris in humans. The compositions of this invention exhibit reduced skin irritation but undiminished effectiveness as compared to prior art retinoic acid-containing topical compositions.

2. Description of Related Prior Art

Retinoic acid, or 3,7-dimethyl-9-(2,6,6-trimethyl-1-cyclohexen-1-yl)-2,4,6,8-nonatetraenoic acid, sometimes known as all-trans retinoic acid, vitamin A acid or tretinoin), has the structural formula:

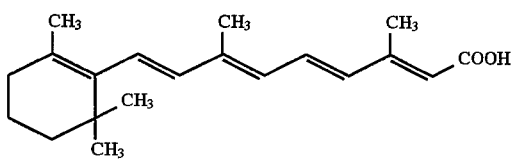

Retinoic acid and like compounds are keratolytic agents, and have been used topically in the treatment of acne vulgaris; see, for example, Kligman U.S. Pat. No. 3,729,568 and Marks U.S. Pat. No. 4,247,547, issued Apr. 24, 1973 and Jan. 27, 1981, respectively.

Retinoic acid and compositions containing it have also been used topically to retard and ameliorate photoageing of skin, especially facial skin, and to retard and reverse the effects of senile keratosis; see, for example, Kligman U.S. Pat. No. 4,603,146, issued Jul. 29, 1986.

Moderate to severe skin irritation can result from the use of retinoic acid and topical prior art compositions containing it for such purposes.

Chess, et al. U.S. Pat. Nos. 4,971,800; 5,045,317 and 5,051,260, issued Nov. 20, 1990, Sep. 3, 1991 and Sep. 24, 1991, respectively, all assigned to The Regents of the University of California and exclusively licensed to the assignee of the present application, disclose compositions comprising hydroxy-terminated urethane penetration enhancing compounds represented by the general formula:

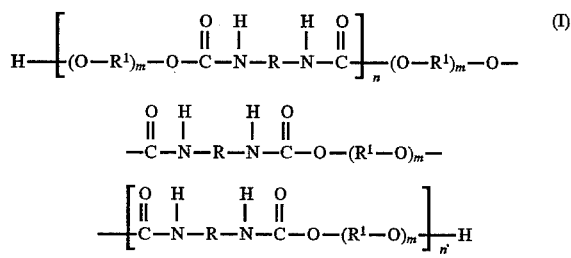

wherein R represents an alkylene or alkenylene radical, generally one containing from about one to about 20 carbon atoms, such as methylene, trimethylene and dimethyltrimethylene radicals, and in the case of the alkenylene radicals, one having between one and about 3 double bonds, or a cycloalkylene or cycloalkenylene radical, generally one containing from about 5 to about 10 carbon atoms, such as cyclopentylene, cyclohexylene and cyclohexenylene radicals, or a mononuclear or fused ring arylene radical, generally one containing from about 6 to about 10 carbon atoms, such as phenylene or naphthylene, all of which can be unsubstituted or substituted, e.g., with alkyl groups, generally ones containing up to about 6 carbon atoms, aryl groups which may be substituted with amine moieties, nitro, lower (1–6 C) alkyl, lower (1–6 C) alkoxy, lower (1–6 C) alkoxy-substituted lower (1–6 C) alkyl, halogen, and the like. $R^1$ represents the same or different alkylene or alkenylene radicals, generally ones containing from about 2 to 6 carbon atoms, such as $-CH_2CH_2-$ and $-CH_2CH_2CH_2-$, and in the case of the alkenylene radicals, ones typically having one or two double bonds; m is an integer selected so as to provide an $-(O-R')-$moiety having a molecular weight of from about 40 to about 6,000, more typically from about 400 to about 2,000, and n and n' are the same or a different integer of from 0 to 30, inclusive, correlated with m so as to provide penetration enhancers for delivering pharmacologically active agents (i.e., "drugs" or "medicaments") to and through the skin said penetration agents having a molecular weight of up to about 60,000, more typically from about 220 to about 37,000, and preferably from about 1,000 to about 10,000–15,000.

SUMMARY OF THE INVENTION

As noted, the above-described urethane compounds are disclosed by Chess, et al. as enhancing the penetration or permeability of human skin by pharmacologically active agents mixed with such compounds. Included among Chess, et al's. "[l]ocally administered topical medicaments" with which such compounds can be administered are "retinoids" and "anti-acne medicaments" see, for example, the Chess, et al. '800 patent at column 5, lines 28–34; but no further identification of such substances is given in the Chess, et al. patents.

In the case of retinoic acid, however, it has now been discovered, quite unexpectedly, that the presence of the above-described urethane compounds can decrease, rather than increase, percutaneous transmission of topically-applied retinoic acid, and leads instead to deposition in the skin of a majority of the retinoic acid applied. Unexpected as well was the discovery that topical application of retinoic acid compositions that also contain these urethane compounds leads to reduced skin irritation but undiminished effectiveness when compared to retinoic acid-containing topical formulations otherwise identical except for the absence of a urethane compound.

Hence, the topically applied retinoic acid compositions of this invention can be used to treat acne vulgaris, to retard and ameliorate photoageing of the skin, especially facial skin, and to retard and reverse the effects of senile keratosis. Because of the reduced itching, burning and peeling of the skin encountered when using the topically applied compositions of this invention, they can also be used to treat a variety of other skin conditions hitherto considered unsuitable for treatment with retinoic acid, such as hyperpigmentation and psoriasis.

It is therefore an object of this invention to provide novel retinoic acid-containing compositions.

It is also an object of this invention to provide retinoic acid-containing topical compositions for use in treating, inter alia, acne vulgaris in humans.

A further object to this invention is to provide novel retinoic acid-containing topical compositions in the form of creams, lotions, gels, and the like, containing specific urethane compounds, which exhibit decreased percutaneous retinoic acid transmission and reduced skin irritation while exhibiting undiminished retinoic acid effectiveness.

A still further object of this invention is to provide novel methods of administering retinoic acid-containing compositions using urethane compounds.

These and other objects, as well as the nature, scope and utilization of this invention, will become readily apparent to those skilled in the art from the following description and the appended claims.

BRIEF DESCRIPTION OF THE DRAWINGS

FIGS. 1 and 2 give the results of the percutaneous penetration of retinoic acid from the three test formulations of Example 1, infra.

FIG. 3 gives the results of the investigator's overall global rating of improvement in acne lesions in patients treated with the three test formulations of Example 3, infra.

FIG. 4 gives the results of the investigator's assessment of erythema in patients treated with the three test formulations of Example 3, infra.

FIG. 5 gives the results of the investigator's assessment of peeling in patients treated with the three test formulations of Example 3, infra.

FIG. 6 gives the results of the investigator's assessment of dryness in patients treated with the three test formulations of Example 3, infra.

FIG. 7 gives the results of the investigator's assessment of skin irritation in patients treated with the test formulations of Example 5, infra.

DETAILED DESCRIPTION OF THE INVENTION

The urethane compounds used in the novel retinoic acid-containing topical compositions of this invention are those recited in the aforementioned Chess, et al. patents. these compounds can be prepared by reacting approximately two moles of a hydroxy-terminated linear alkylene or polyalkylene glycol or polyether with approximately one mole of a monomeric organic diisocyanate.

The hydroxy-terminated linear alkylene or polyalkylene glycols or polyethers used in this reaction are ones represented by the formula:

wherein R' and m are as defined hereinabove for formula I. Included among these alkylene or polyalkylene glycols or polyethers are ethylene glycol, propylene glycol, butylene glycol and the like; polyalkylene ether glycols, such as polyethylene glycols, polypropylene glycols, polybutylene glycols, polytetramethylene glycols, polyhexamethylene glycols, polypropenylene glycols, and the like, which are obtained, for example, by acid-catalyzed condensation of lower alkylene oxides, such as ethylene oxide, propylene oxide, and the like, either with themselves or with glycols such as ethylene glycol, propylene glycol, propenylene glycol, and the like.

Polyalkylenearylene ether glycols which also have a molecular weights ranging from about 40 to about 6000, more typically from about 400 to about 2,000, but which differ from the above-described polyalkylene glycols in having cycloalkylene or cycloalkenylene radicals, generally ones which contain from about 5 to about 10 carbon atoms, such as cyclopentylene, cyclohexylene, and cyclohexenylene radicals, or mononuclear or fused ring arylene radicals, all of which may either be unsubstituted or substituted, e.g., with alkyl groups, generally ones containing up to about 6 carbon atoms, amine groups, nitro groups, lower alkoxy and lower alkoxy-substituted lower (1–6C) alkyl groups, halogens, and the like, in place of some of the alkylene or alkenylene radicals of said polyalkylene glycols, may also be employed as polyalkylene glycol or polyether reactants.

Specific polyalkylene glycol or polyether reactants coming within the scope of formula II hereinabove include:

diethylene glycol,
triethylene glycol,
polyethylene glycol 300,
polyethylene glycol 400,
polyethylene glycol 600,
polyethylene glycol 900,
polyethylene glycol 1000,
polyethylene glycol 2000,
polypropylene glycol 400,
polypropylene glycol 700,
polypropylene glycol 1000,
polypropylene glycol 1200,
polypropylene glycol 2000,
polypropylene glycol 3000,
polypropylene glycol 4000,
polypropylene glycol 6000,
polytetramethylene glycols having molecular weights ranging from about 600 to 6000, and the like.

As can readily be appreciated, mixtures of the various reactive organic polyalkylene glycols or polyethers described hereinabove may also be employed in preparing the nonpolymeric hydroxy- or alkoxy-terminated urethan compounds used in the practice of the present invention.

A wide variety of monomeric organic diisocyanates represented by the general formula:

wherein R is as defined hereinabove for formula I, can be used to form these compounds. Included among such diisocyanates, such as m-phenylenediisocyanate, p-phenylenediisocyanate, 4-t-butyl-m-phenylenediisocyanate, 4-methoxy-m-phenylenediisocyanate, 4-phenoxy-m-phenylenediisocyanate, 4-chloro-m-phenylenediisocyanate, toluenediisocynates (either as a mixture of isomers, e.g., the commercially available mixture of 80% 2,4-toluenediisocyanate and 20% 2,6-toluenediisocyanate, or as the individual isomers themselves), m-xylylenediisocyanate, p-xylylenediisocyanate, 1,4-naphthylenediisocyanate, 1,5-naphthylenediisocyanate, 1,8-naphthylenediisocyanate, 2,6-napthylenediisocyanate, 1,5-tetrahydronaphthylenediisocyanate, p,p'-diphenyldiisocyanate, diphenylmethane-4,4'-diisocyanate, 2,4-diphenylhexane-6,6-diisocyanate, "bitolylenediisocyanate" (3,3'dimethyl-4,4'-biphenylenediisocyanate), "dianisidinediisocyanate" (3,3'-dimethoxy-4,4'-biphenylenediisocyanate); aliphatic diisocyanates, such as methylenediisocyanate, ethylenediisocyanate, the tri-, tetra-, penta-, hexa-, octa-, nona- and decamethylene-Ω, Ω-diisocyanates, 2-chloro-trimethylenediisocyanate, 2,3-dimethyltetramethylenediisocyanate, and the like as well as mixtures thereof.

Methods of synthesizing urethanes have long been known in the art. U.S. Pat. No. 2,266,777, for example, issued in 1941, describes the reaction of isocyanate compound with polyhydroxy alcohols to give polyurethanes, now a standard synthetic method. Reference may also be had to Saunders, "Polyurethanes: Chemistry and Technology" (New York: Wiley & Sons, 1961) for an overview of the chemistry of urethanes.

In preparing the urethane compound of formula I, the mole ratio of diol to diisocyanate is about 2:1, and the reaction is carried out at elevated temperature (at least about 100° F. and preferably at least about 150° F.; temperatures may be higher depending on the particular reactants and on the amount of catalyst used with constant mixing. Solvents such as hydrocarbon solvents, e.g., dioxane, xylene, cyclohexane, or the like, can be used. The use of catalysts is optional, but catalysts such as organic tin alkyl titanates or octoates, amines such as those in the Dabco group (i.e., Dabco DC-1, DC-2, R-8020, R-595, 33 LV, DF and WT, all available from Air Products and Chemicals, In., Allentown, Pa., U.S.A., under the "Dabco" trademark) and N-ethyl morpholine, and the like can be used if desired. Further information regarding analogous reactions may be found in U.S. Pat. Nos. 2,266,777 and 2,282,827, the disclosures of which are incorporated by reference herein in their entirety.

The values of n and n' for the compound of Formula I may be controlled during synthesis by varying the reaction temperature, the amount, if any, of water in the reaction mixture, and the starting materials. For example, a higher temperature will typically result in a more highly polymerized structure, i.e., one having a higher m value, while increasing the amount of water present will ordinarily give different molecular weight compound. Selection of reaction conditions herein is believed to be well within the skill of the art, and may in any case be readily derived from the aforementioned references on urethane chemistry.

The molecular weights of the urethane compounds used in practicing this invention can be determined on a Waters Associates (Milford, Mass., U.S.A.) liquid chromatograph consisting of a Model 510 pump, a U6K sample ejector and a Model 410 refractive index detector. Typically, the column set is one 1000 Å and two 500 Å Ultrastyragel gel permeation chromatography columns, each 7 mm inside diameter and 30 cm in length. Tetrahydrofuran, pumped at a flow rate of 1.0 ml/min. is the solvent. The system is microcomputer controlled using Maxima 820 software supplied by Dynamic Solutions (a division of Waters Associates).

Calibration of the column set is performed using polypropylene glycol standards (Scientific Polymer products, Inc., Ontario, N.Y., U.S.A.) for molecular weights below 4,000 daltons, and polystyrene for molecular weights up to 200,000 daltons. All molecular weights are referenced to the calibration with these standards. Samples are prepared as 0.1% (1000 ppm) solutions in tetrahydrofuran, and 100 ul of the thus-prepared solutions are injected for each analysis.

A typical urethane compound can be one prepared by reacting two moles of polypropylene glycol 725 with one mole of dicyclohexylmethane diisocyanate at a temperature of about 150° F. to 160° F. for about 80–100 minutes, with stirring, in the presence of a catalytic amount of stanous octoate, then cooling to room temperature (about 25° F.); see the Chess, et al. '800 patent, Examples 1 and 5. A chromatogram of such an compound shows it to have, based on uncorrected peak areas of the chromatogram, fractions falling within the following ranges:

| Peak | Composition* | |
|---|---|---|
| 1 | PPG-I-PPG | 25–35% |
| 2 | PPG-I-PPG-I-PPG | 18–30% |
| 3 | PPG-I-PPG-I-PPG-I-PPG | 14–22% |
| 4 | larger compoundic species | 10–30% |

*/PPG = polypropylene glycol, average molecular weight = about 725; I = dicyclohexylmethane diisocyanate.

An "effective" amount of urethane compound as used herein means an amount of at least about 1 percent by weight, based on the total weight of the composition. In general, however, the amount of urethane compound used can range from about 1 to about 20 percent by weight, and preferably from about 2 to about 15 percent by weight, based on the total weight of the formulation.

The amount of retinoic acid that will be employed in formulating the novel topical compositions of this invention can vary within significant limits, depending on the therapeutic use for which the composition will be applied to the skin. This amount will most often range, however, from about 0.001 to about 3.0 percent by weight, and preferably from about 0.025 to about 0.5 percent by weight, based on the total weight of the composition, when the composition is used to treat acne vulgaris. When the composition is used to treat the effects of aging and sun damage on the skin, the amount of retinoic acid will generally range from about 0.001 to about 3.0 percent by weight, and preferably from about 0.025 percent to about 0.5 percent by weight, based on the total weight of the composition.

Retinoic acid-containing compositions formulated in accordance with this invention to contain one or more of these hydroxy-terminated urethane compounds will also contain one or more topical carriers. The term "topical carrier" as used herein refers to a carrier material suitable for topical applications of formulations containing retinoic acid, and encompasses any such carrier materials known in the cosmetic and medical arts. Included within suitable topical carriers for use in practicing this invention are liquid and nonliquid gels, creams, ointments, lotions, emulsions, solvents, liquid diluents, and the like as well as mixtures thereof, which do not themselves adversely affect living mammalian tissue or interact with other components of the retinoic acid-containing composition in a deleterious manner. Topical carriers are used to provide the formulations of this invention in their preferred liquid, cream or semiliquid (gel) forms. Suitable topical carriers for use in practicing this invention include water, liquid alcohols, e.g., ethanol and isopropanol, liquid glycols, liquid polyalkylene glycols, liquid esters, liquid amides, liquid protein hydrolysates, liquid alkylated protein hydrolysates, liquid lanolin and lanolin derivatives, and like materials, as well as mixtures thereof.

In order that those skilled in the art can more fully understand this invention, the following examples are set forth. These examples are given solely for purposes of illustration, and should not be considered as expressing limitations unless so set forth in the appended claims. All parts and percentages are by weight unless otherwise stated.

EXAMPLE 1

(In Vitro Percutaneous Penetration Studies)

A retinoic acid (0.025%) containing formulation also containing 10% of a urethane compound, Formulation A, was evaluated and compared to a retinoic acid (0.025%) containing formulation without the urethane compound, Formulation B, and Retin-A® gel (0.025% retinoic acid; Ortho Pharmaceuticals). Formulas A and B contained the following ingredients.

TABLE I

| Component[1] | A | B |
| --- | --- | --- |
| Retinoic Acid | 0.025 | 0.025 |
| Ethanol | 88.165 | 98.165 |
| Urethane Compound[2] | 10.00 | 0.00 |
| Hydroxypropyl cellulose | 1.80 | 1.80 |
| Butylated hydroxytoluene | 0.01 | 0.01 |

[1] Quantities in grams per 100 grams
[2] The urethane compound used in this example has an average molecular weight of about 4000 and was prepared by reacting about one mole of dicyclohexylmethanediisocyanate with about two moles of polypropylene glycol 725.

The in vitro methodology of the FDA and AAPS Report of the Workshop on Principles and Practices of In Vitro Percutaneous Studies (Pharm. Res. 4:265, 1987) was followed. Human cadaver skin dermatomed to 0.6 mm was kept frozen until thawed for the experiment. Twenty-one Franz-type flow-through diffusion cells, as modified by Bronaugh and Stewart (J. Pharm. Sci., 74:64, 1985) (Crown Glass), were used. The flow cells were placed in water jacketed holding blocks, mounted over an ISCO fraction collector, and thermoregulated with 37° C. water pumped through the blocks.

The test formulations were prepared for a desired specific activity of 3600 disintegrations per minute (DPM)/ng total retinoic acid (radiolabeled and unlabeled). Each formulation (300 mg) was spiked with 30 µL of retinoic acid ethanolic stock solution (121 µCi retinoic acid). The stock solution was transferred to the bottom of each of three 12×75 mm test tubes and the ethanol was evaporated under a gentle stream of nitrogen. The appropriate non-radiolabeled ethanolic gel formulation was added to the bottom of the test tube and the label was incorporated into the formulation by vortexing intermittently for one hour at 4° C. The formulations were maintained at about 4° C. at all times to minimize evaporative loss of ethanol in the gel.

A tube containing about 300 mg non-radiolabeled formulation was prepared and treated (vortexed) in parallel to the radiolabeled formulations. Five 5 µL aliquots of the non-radiolabeled formulation were weighed with an accuracy of 0.01 mg. The specific gravity (mg/µL) of each formulation was determined and the volume (µL) per 3.18 mg of formulation was calculated.

Five aliquots (equal to 3.18 mg) of each radiolabeled formulation was transferred into glass scintillation vials, dissolved completely in scintillation cocktail and counted in a Packard 1600CA liquid scintillation analyzer. The mean, standard deviation (SD) and the % coefficient of variation (% CV) DPM per 3.18 mg of formulation were calculated. The formulations were judged to have been adequately mixed if the % C.V. was less than 10%. The DPM/ng retinoic acid was then calculated.

Each skin sample was dosed with 3.18 mg (5.0 mg/cm$^2$) of formulation. The flow cell effluent (degassed phosphate buffered saline/1.5% Oleth, 290 mOsm, pH 7.4) was set to 0.9 ml/hour, and the flow cell effluent was collected via fraction collector every 8 hours up to 40 hours. 10 mLs Ready Gel™ was added to each of the percutaneous penetration samples and one blank control sample (8 mLs effluent). The sample vials were counted in a Packard 1600 CA liquid scintillation analyzer.

The results of the percutaneous penetration of retinoic acid from the three test formulations are given in FIGS. 1 and 2. Specifically, the penetration rate, the amount as obtained in this example of retinoic acid passing into the receptor fluid (effluent) per hour, is presented in FIG. 1, with the rate being plotted at the end of each collection interval, while FIG. 2 shows the cumulative retinoic acid that penetrated the skin, with the amount being plotted at the end of each collection period.

As can be seen from the results of this example, the retinoic acid formulation without the urethane compound present has retinoic acid percutaneous penetration properties that are comparable to those of Retin-A® gel. The retinoic acid formulation without the compound present and Retin-A® gel showed, and significantly greater retinoic acid percutaneous penetration than the retinoic acid formulation containing the urethane compound.

EXAMPLE 2

This experimental procedure was carried out to identify the distribution of radioisotope in the cadaver skin of Example 1, and to account for the radiolabeled dose of retinoic acid (mass balance).

The surface of each skin sample was 'stripped' sequentially 4 times with Thrifty™ transparent mending tape to remove any remaining formulation and the most superficial portion of the stratum corneum. The pieces of tape were then placed in one glass vial. The epidermis was mechanically separated from the dermis using surgical forceps, and the skin sections were each placed in labeled glass vials. Two mLs of saponification solution (45% KOHN in EtOH) were added to each scintillation vial. A counting blank of 2 mLs saponification solution was prepared and included with the samples. All vials were set in a 65° C. water bath for 3 hours, after which they were removed and brought to room temperature. 2.5 mLs of 1.28N HCl was added to each saponified sample vial and agitated slightly. Deionized water (6 mLs) was added to each sample and shaken well. 10 mLs Ready Gel™ was added to each sample. The samples were then counted on the Packard 1600 CA liquid scintillation counter.

Each flow cell, screw closure and exit port was placed in a cup containing ~75 mLs 0.1% Alconox solution after removal of the skin sample. The cups were agitated slightly and allowed to sit for 1 hour. The cell was then rinsed into the wash cup with a few mLs of deionized water. The amount of wash solution in the cup was determined. Two 1 ml aliquots were taken from each wash cup and placed into glass scintillation vials. 2.0 mLs Ready Gel™ was added to each vial. All vials were counted in the Packard 1600 CA liquid scintillation analyzer.

The results of this localization analysis are given in Table II.

TABLE II

Distribution of Recovered Radioactivity (Total = 100%) and the % Theoretical Recovered.

| Treatment | Wash | Dry Wipe | Tape Strip | SC + Epidermis | Dermis | Receptor | % Theoretical Recovered |
|---|---|---|---|---|---|---|---|
| Retin-A ® | 5.16 ± 6.73 | 0.45 ± 0.12 | 75.51 ± 8.95 | 18.31 ± 6.60 | 0.16 ± 0.06 | 0.43 ± 0.05 | 87.27 ± 3.54 |
| Formula B | 3.93 ± 2.29 | 0.51 ± 0.19 | 67.42 ± 4.66 | 27.38 ± 5.42 | 0.35 ± 0.10 | 0.44 ± 0.07 | 82.45 ± 5.91 |
| Formula A | 4.65 ± 3.08 | 0.97 ± 0.25 | 28.19 ± 15.26 | 64.58 ± 13.29 | 1.30 ± 1.72 | 0.33 ± 0.06 | 87.07 ± 5.85 |

The penetration data indicate that the retinoic acid formulation without the urethane compound [Vehicle (control)] has retinoic acid percutaneous penetration properties that are comparable to those of the commercially prepared gel, Retin-A® gel. The retinoic acid formulation containing the urethane compound (Formula A) showed significantly less retinoic acid percutaneous penetration than the vehicle (control) and Retin-A® gel. Moreover, the localization data indicate that the inclusion of 10% are results in an increase in the distribution of retinoic acid into the epidermis.

EXAMPLE 3

(Treatment of Acne in Humans)

A double blind, random, parallel group study using Formulation A and Retin-A® gel, as in Example 1, and the vehicle of Formulation A (retinoic acid absent, urethane compound present; Formula B), was carried out. Two hundred fifteen patients were randomized to one of three treatment groups, each of which groups received one of the three test substances once each night for 12 weeks. The patents were evaluated at days 0, 7, 14, 28, 56 and 84.

The efficacy of the three substances tested was evaluated by comparing the three groups with respect to mean lesion count, mean percent change in lesion count, and categorical percent improvement in lesion count. These analyses were done for total lesion counts, for non-inflammatory lesion counts, and for inflammatory lesion counts. An additional evaluation was the physician's overall global rating of improvement; FIG. 3.

Safety was evaluated by comparing the treatments in respect to the physician's evaluation of erythema, peeling and dryness; FIGS. 4–6.

Formulation A with 10% urethane compound is equivalent to Retin-A® gel for efficacy in the treatment of acne. Both Formulation A and Retin-A® gel are superior in efficacy relative to the vehicle (control) formulation. However, as can be seen from FIGS. 4–6, Formulation A with 10% urethane compound causes less peeling (FIG. 4), dryness (FIG. 5), and erythema (FIG. 6) than does Retin-A® gel.

EXAMPLE 4

(Human Skin Irritation Study with Gel Formulations)

A retinoic acid (0.025%) containing gel formulation, Formulation A, containing 10% of the urethane compound of Example 1, was evaluated and compared to Retin-A® gel (0.025% retinoic acid; Ortho Pharmaceuticals), and Formulation A's vehicle (without the urethane compound) as a control.

18 female panelists were used in the study. Subjects with acne, skin diseases (e.g. psoriasis or eczema), abrasions, scare tissue, or tattoos at the test sites were excluded from participation, as was anyone using antihistamines or corticosteroids.

Test patches containing 0.1 to 0.3 ml of the assigned formulation were prepared. Each panelist received three 24 hour contact applications of patches containing each formulation to sites on the upper back. All patch applications and removals were conducted by a technician. All skin sites were scored within 30 minutes after removal of the patch.

Measurement of irritation was conducted by an experienced staff member using a 100 watt incandescent blue bulb lamp as the artificial light source to illuminate the patch areas. The scorer was kept uninformed of treatment assignments and any previous scores. The same individual did all of the measurements during the course of the study.

The results of this study are given in Table III,

TABLE III

Primary Irritation in Humans; Retinoic Acid Gel
Mean Irritation Scores produced in a panel of 18 Subjects Under Occlusion

| | Mean Irritation Score ± Standard Deviation | |
|---|---|---|
| Test Substance | One Application | Three Applications |
| Retin-A ® gel (0.025% retinoic acid) | 2.89 ± 0.96 | 15.0 ± 3.56 |
| Retinoic Acid Gel (0.025%) containing 10% urethane compound | 0.61 ± 1.29 | 1.61 ± 2.06 | and illustrate that the 0.025% retinoic gel formulation having 10% urethane oligomer causes less skin irritation than 0.025% Retin-A® gel.

EXAMPLE 5

(Human Skin Irritation Study with Cream Formulations)

Retinoic acid (0.025, 0.05 and 0.1%) cream formulations containing urethane compound, according to the present invention, were evaluated and compared to Retin-A® gel cream formulations (0.025, 0.05, and 0.10% retinoic acid containing formulations by Ortho Pharmaceuticals). At the two low concentrations of retinoic acid, the experimental formulations contained 20% urethane compound. At the 0.1% concentration of retinoic acid three levels of urethane oligomer were evaluated (10, 15, and 20%).

The formulations are given below:

TABLE IV

Retinoic Acid Cream Formulations

| Ingredients | | | | | |
|---|---|---|---|---|---|
| Water | 52.30 | 47.30 | 42.30 | 42.35 | 42.38 |
| Urethane compound | 10.00 | 15.00 | 20.00 | 20.00 | 20.00 |
| Stearic acid | 19.00 | 19.00 | 19.00 | 19.00 | 19.00 |
| Isopropyl Myristate | 10.00 | 10.00 | 10.00 | 10.00 | 10.00 |
| Polyoxyl 40 stearate {Myrj 52S} | 5.00 | 5.00 | 5.00 | 5.00 | 5.00 |
| Stearyl Alcohol | 3.00 | 3.00 | 3.00 | 3.00 | 3.00 |
| Sorbic acid | 0.20 | 0.20 | 0.20 | 0.20 | 0.20 |
| Xanthan gum {Keltrol T} | 0.30 | 0.30 | 0.30 | 0.30 | 0.30 |
| BHT | 0.10 | 0.10 | 0.10 | 0.10 | 0.10 |
| Retinoic Add | 0.10 | 0.10 | 0.10 | 0.05 | 0.025 |
| | 100.00 | 100.00 | 100.00 | 100.00 | 100.00 |

The urethane compound was that used in Example 1.

18 female panelists were used in the study. Subjects with acne, skin diseases (e.g. psoriasis or eczema), abrasions, scar tissue, or tattoos at the test sites were excluded from participation, as was anyone using antihistamines or corticosteroids.

Test patches containing 0.1 to 0.3 ml of the assigned formulation were prepared. Each panelist received three 24 hour contact applications of patches containing each formulation to sites on the upper back. All patch applications and removals were conducted by a technician. All skin sites were scored within 30 minutes after removal of the patch.

Measurement of irritation was conducted by an experienced staff member using a 100 watt incandescent blue bulb lamp as the artificial light source to illuminate the patch areas. The scorer was kept uninformed of treatment assignments and any previous scores. The same individual did all of the measurements during the course of the study.

The results are given in FIG. 7 and illustrate that the retinoic acid (0.025, 0.05, and 0.1%) containing cream formulations with urethane compound present cause less skin irritation than Retin-A® creams.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. A topical composition comprising:
   (a) retinoic acid in an amount effective to treat acne vulgaris or the effects of senile keratosis or photoageing of the skin;
   (b) an amount of a urethane compound having a molecular weight of up to about 60,000, prepared by reacting approximately two moles of a hydroxy-terminated linear alkylene or polyalkylene glycol or polyether with approximately one mole of a monomeric organic diisocyanate, sufficient to permit the topical composition to exhibit reduced skin irritation but undiminished effectiveness as compared to a composition otherwise identical except for the absence of the urethane compound; and
   (c) an amount of a topical carrier sufficient to provide said topical composition in the form of a liquid, a cream or a gel.

2. A topical composition as recited in claim 1 wherein the urethane compound is represented by the general formula:

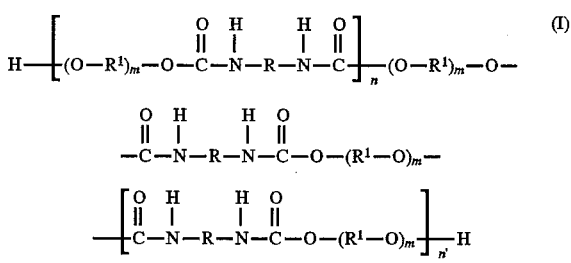

wherein R represents an alkylene or alkenylene radical, a cycloalkylene or cycloalkenylene radical, or a mononuclear or fused ring arylene radical, all of which can be unsubstituted or substituted, $R^1$ represents the same or different alkylene or alkenylene radicals, m is an integer selected so as to provide an $-(O-R')-$ moiety having a molecular weight of from about 40 to about 6,000, and n and n' are the same or a different integer of from 0 to 30, inclusive, correlated with m so as to provide a urethane compound having a molecular weight of up to about 60,000.

3. A topical composition as recited in claim 2 wherein the urethane compound has a molecular weight of from about 1,000 to about 15,000.

4. A topical composition as recited in claim 2 wherein the urethane compound is prepared by reacting about one mole of dicyclohexylmethanediisocyanate with about two moles of propylene glycol 725, and has a molecular weight of about 4,000.

5. A topical composition as recited in any one of claims 1, 2, 3, or 4 in the form of a liquid.

6. A topical composition as recited in any one of claims 1, 2, 3, or 4 in the form of a gel.

7. A topical composition as recited in any one of claims 1, 2, 3, or 4 in the form of a cream.

* * * * *

UNITED STATES PATENT AND TRADEMARK OFFICE
CERTIFICATE OF CORRECTION

PATENT NO. : 5,650,171
DATED : July 22, 1997
INVENTOR(S) : Quigley, et. al.

It is certified that error appears in the above-identified patent and that said Letters Patent is hereby corrected as shown below:

On the cover page of the patent, a portion of the diagram reads "mg/cm$^2$2/HR." This should read --ng/cm$^2$/HR--.

Fig. 1, a portion of the diagram reads "mg/cm$^2$2/HR." This should read --ng/cm$^2$/HR--.

Fig. 7, "RETINOLE ACID" should read --RETINOIC ACID--.

Column 2, line 31, "[l]ocally" should read --locally--.

Column 10, line 13, "scare tissue" should read --scar tissue--.

Column 12, line 44, "propylene" should read --polypropylene--.

Signed and Sealed this

Fifteenth Day of December, 1998

*Attest:*

*Attesting Officer*

BRUCE LEHMAN

Commissioner of Patents and Trademarks